US012193882B2

(12) United States Patent
Aladahalli et al.

(10) Patent No.: US 12,193,882 B2
(45) Date of Patent: Jan. 14, 2025

(54) SYSTEM AND METHODS FOR ADAPTIVE GUIDANCE FOR MEDICAL IMAGING

(71) Applicant: GE Precision Healthcare LLC, Milwaukee, WI (US)

(72) Inventors: Chandan Kumar Mallappa Aladahalli, Bangalore (IN); Krishna Seetharam Shriram, Bangalore (IN); Vikram Melapudi, Bangalore (IN)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 112 days.

(21) Appl. No.: 17/209,080

(22) Filed: Mar. 22, 2021

(65) Prior Publication Data

US 2022/0296219 A1 Sep. 22, 2022

(51) Int. Cl.
*A61B 8/00* (2006.01)
*A61B 8/08* (2006.01)
*G06T 7/10* (2017.01)

(52) U.S. Cl.
CPC .............. *A61B 8/54* (2013.01); *A61B 8/4263* (2013.01); *A61B 8/463* (2013.01); *A61B 8/52* (2013.01); *G06T 7/10* (2017.01); *G06T 2207/10132* (2013.01); *G06T 2207/20081* (2013.01); *G06T 2207/30004* (2013.01)

(58) Field of Classification Search
CPC ......... A61B 8/54; A61B 8/4263; A61B 8/463; A61B 8/52; A61B 8/4245; G06T 7/10; G06T 2207/10132; G06T 2207/20081; G06T 2207/30004; G06T 7/00
See application file for complete search history.

(56) References Cited

U.S. PATENT DOCUMENTS

| | | | |
|---|---|---|---|
| 10,964,424 B2 | 3/2021 | Pagoulatos et al. | |
| 2017/0086785 A1 | 3/2017 | Bjaerum | |
| 2018/0153505 A1 | 6/2018 | Cadieu et al. | |
| 2020/0069285 A1* | 3/2020 | Annangi | A61B 8/5207 |
| 2020/0196984 A1* | 6/2020 | Sprung | A61B 8/483 |
| 2020/0245970 A1 | 8/2020 | Cadieu et al. | |
| 2020/0375546 A1 | 12/2020 | Shoudy et al. | |
| 2020/0375571 A1* | 12/2020 | Lorraine | A61B 8/4254 |
| 2021/0038321 A1* | 2/2021 | Toporek | A61B 8/54 |

(Continued)

OTHER PUBLICATIONS

Ajitjaokar. (Oct. 27, 2019.) Understanding the applications of Probability in Machine Learning. Data Science Central. https://www.datasciencecentral.com/understanding-the-applications-of-probability-in-machine-learning/. (Year: 2019).*

(Continued)

*Primary Examiner* — Angela M Hoffa
*Assistant Examiner* — Younhee Choi
(74) *Attorney, Agent, or Firm* — McCoy Russell LLP

(57) ABSTRACT

Methods and systems are provided for generating user guidance for ultrasound imaging. In one example, a method includes determining, with a probe recommendation model, a user action to an ultrasound probe prior to and/or during acquisition of a current ultrasound image frame, one or more anatomical features in the current ultrasound image frame, and an anatomy view of the current ultrasound image frame, and outputting, for display on a display device, a probe motion recommendation based on the user action, the one or more anatomical features, and the anatomy view.

19 Claims, 8 Drawing Sheets

(56) References Cited

U.S. PATENT DOCUMENTS

| | | | |
|---|---|---|---|
| 2021/0052253 A1 | 2/2021 | Cadieu et al. | |
| 2021/0272679 A1 | 9/2021 | Pagoulatos et al. | |
| 2021/0369249 A1* | 12/2021 | Toporek | A61B 8/467 |
| 2022/0175345 A1* | 6/2022 | Kasahara | A61B 8/4254 |

OTHER PUBLICATIONS

Baum, "Machine learning for ultrasound-guided interventions," Abstract, University College London, accessed on Jun. 22, 2021, [https://gtr.ukri.org/projects?ref=studentship-2361326#/tabOverview], 4 pages.

Preiswerk, "Deep learning for ultrasound transducer tracking," Harvard University, accessed on Jun. 22, 2021, [https://scholar.harvard.edu/frank/deep-learning-ultrasound-transducer-tracking-0], 2 pages.

Sun, S., "Ultrasound Probe Localization by Tracking Skin Features," MIT Libraries Website, Available Online at https://dspace.mit.edu/handle/1721.1/93069, Sep. 2014, 141 pages.

Prevost, R. et al., "3D freehand ultrasound without external tracking using deep learning," Medical Image Analysis, vol. 48, Aug. 2018, 16 pages.

Baum, Z. et al., "Machine learning for ultrasound-guided interventions," UK Research and Innovation Website, Available Online at https://gtr.ukri.org/projects?ref=studentship-2361326, Available as Early as Sep. 19, 2020, 3 pages.

* cited by examiner

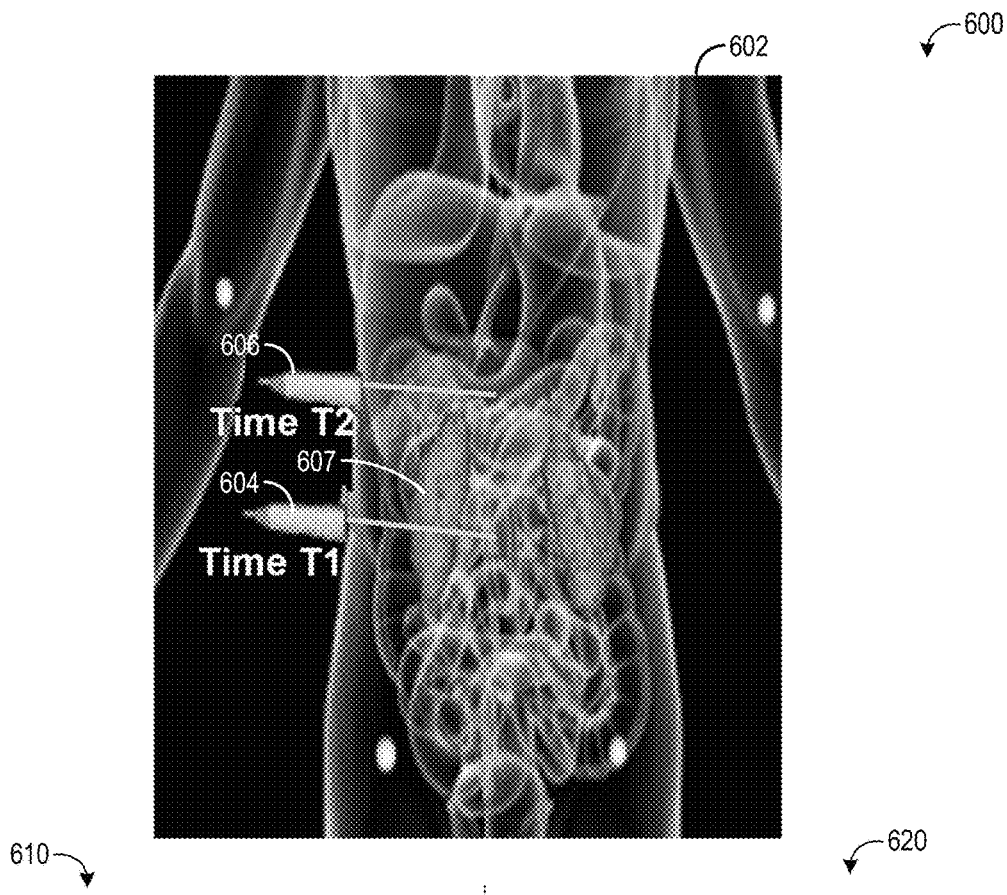

| Without User Action Detection | With User Action Detection |
|---|---|
| Time T1: <br> • <u>Anatomy view</u>: lower pole of kidney <br> • <u>Guidance Feedback</u>: translate/move up | Time T1: <br> • <u>Anatomy view</u>: lower pole of kidney <br> • <u>User action</u>: rotation <br> • <u>Guidance Feedback</u>: translate/move up |
| Time T2: <br> • <u>Anatomy view</u>: no kidney <br> • <u>Guidance Feedback</u>: locate kidney | Time T2: <br> • <u>Anatomy view</u>: no kidney <br> • <u>User action</u>: translating up <br> • <u>Guidance Feedback</u>: translate down |

FIG. 6

SYSTEM AND METHODS FOR ADAPTIVE GUIDANCE FOR MEDICAL IMAGING

TECHNICAL FIELD

Embodiments of the subject matter disclosed herein relate to medical imaging, and more particularly, to improving imaging guidance during medical imaging.

BACKGROUND

Medical ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Ultrasound images of the internal structures may be saved for later analysis by a clinician to aid in diagnosis and/or displayed on a display device in real time or near real time.

SUMMARY

In one embodiment, a method includes determining, with a probe recommendation model, a user action to an ultrasound probe prior to and/or during acquisition of a current ultrasound image frame, one or more anatomical features in the current ultrasound image frame, and an anatomy view of the current ultrasound image frame, and outputting, for display on a display device, a probe motion recommendation based on the user action, one or more anatomical features, and the anatomy view.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which:

FIG. 6 schematically shows example probe motion recommendations.

DETAILED DESCRIPTION

Figure 1:
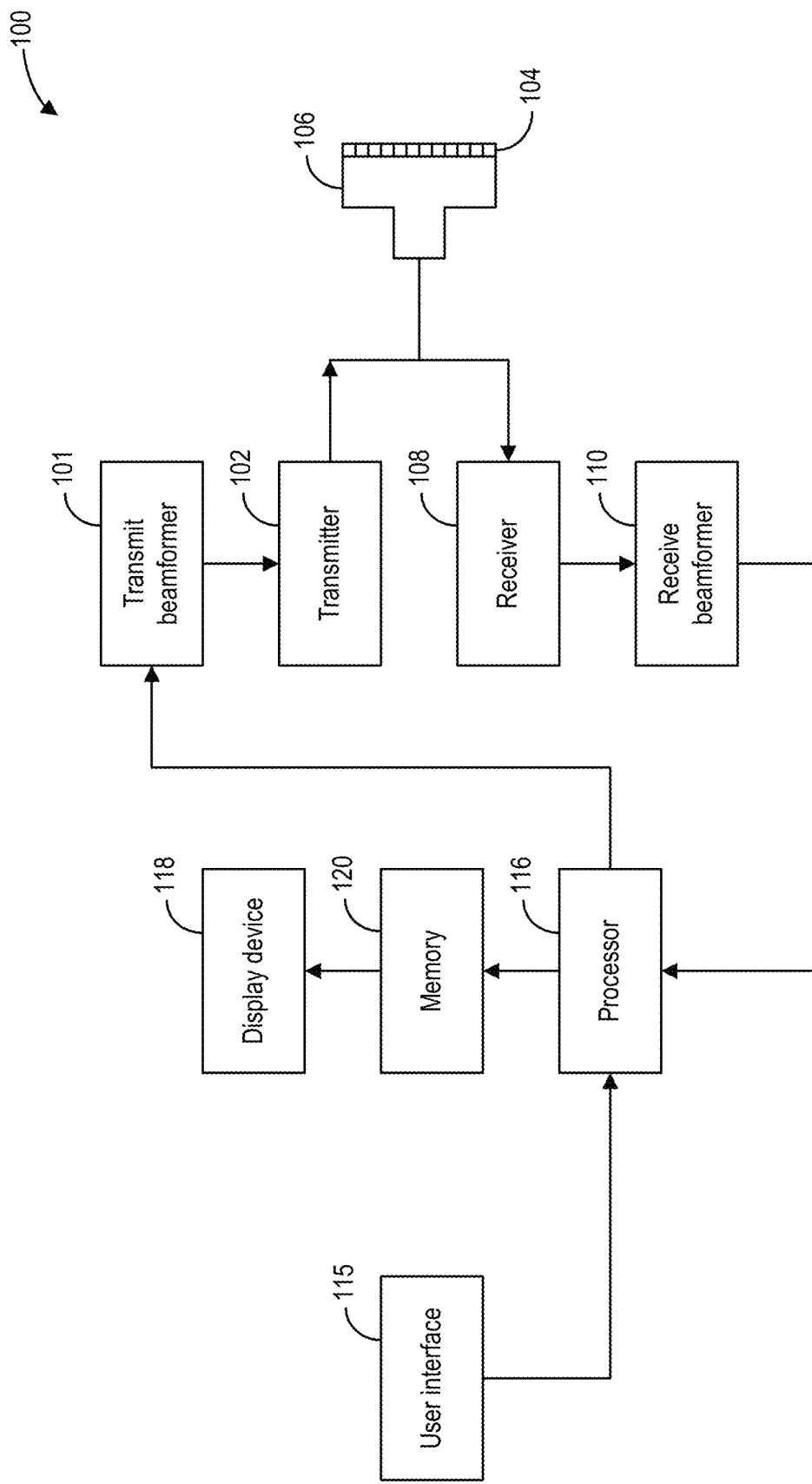
FIG. 1 shows a block diagram of an embodiment of an ultrasound system.

Medical ultrasound imaging typically includes the placement of an ultrasound probe including one or more transducer elements onto an imaging subject, such as a patient, at the location of a target anatomical feature (e.g., abdomen, chest, etc.). Images are acquired by the ultrasound probe and are displayed on a display device in real time or near real time (e.g., the images are displayed once the images are generated and without intentional delay). The operator of the ultrasound probe may view the images and adjust various acquisition parameters and/or the position of the ultrasound probe in order to obtain high-quality images of one or more target anatomical features (e.g., the heart, the liver, the kidney, or another anatomical feature).

Moving the ultrasound probe to the proper location to acquire images of the target anatomical feature(s) can be very challenging and is based on user experience. Thus, probe motion guidance may be provided to aid the operator of the ultrasound probe to properly position the ultrasound probe. Traditional approaches to guidance of ultrasound probe position have relied on zeroth order information about the current view or the current position of the probe. Typically this involves estimating the probe position (e.g., based on anatomical features identified in a current image frame) and recommending probe movement based on the estimated probe position relative to a target probe position.

However, estimating current probe position based solely on the current anatomical view can be challenging and prone to noise, particularly if identifiable anatomical features are not present in the current image. Without taking into account the prevailing user action of the probe (e.g., sliding, tilting, rocking, or rotating the probe) at the time of or just prior to image acquisition, the guidance that is provided on how to move or position the probe may be inaccurate. Also, these methods do not check whether the operator is following the probe movement recommendation and appropriately provide meta-feedback. For example, the frequency of probe motion recommendations is closely connected to whether the user is following the probe motion recommendations or not. Since there is no estimation of whether the user is following the provided recommendations, the recommendations could lead to being stuck in undesirable loops of recommendations and actions.

Thus, according to embodiments disclosed herein, probe motion/placement recommendations may be generated using a user action to the ultrasound probe and a current anatomy view in a joint fashion, from a sequence of ultrasound image frames. For example, one or more machine learning (e.g., deep learning network) models may be trained to generate probe motion recommendations using an estimated user action and a current anatomy view as inputs. In one example, a single model/network may be trained to output probe motion recommendations using the estimated user action and the current anatomy view as inputs. In other examples, separate models/networks may be trained to generate the estimated user action and the current anatomy view, and these may be entered as inputs to another model/network or otherwise used to determine the probe motion recommendations.

The disclosed system may generate robust and accurate probe motion recommendations, as the joint estimation has the advantage of being robust to noise, thus improving accuracy of the guidance. In some examples, the estimation of the user action can be used to check if the user is following the guidance and the frequency of the probe motion recommendations may be changed if warranted. Further, estimating the user action allows the guidance to include negative actions, such as to stop moving the probe or stop rotating the probe, which would not be possible to generate without knowing the current action. Additionally, estimating the user action may help lessen the learning curve for a novice user and help in tuning and improving the guidance/probe motion recommendations. Comparing the user action to the provided probe motion recommendation and the outcome can help identify new data for actively learning of the guidance deep learning network. For example, if the user action is consistently different from the provided guidance, the guidance model may be incorrectly predicting on that frame (e.g., particular anatomical view) and that frame (e.g., anatomical view) may be added to the training set in order to tune or refine the guidance model. Additionally or alternatively, the output guidance may be incorrect as to how to reach the particular scan plane and the user may prefer a different trajectory to get to the target scan plane, which may be used to tune the guidance model.

Figure 2:
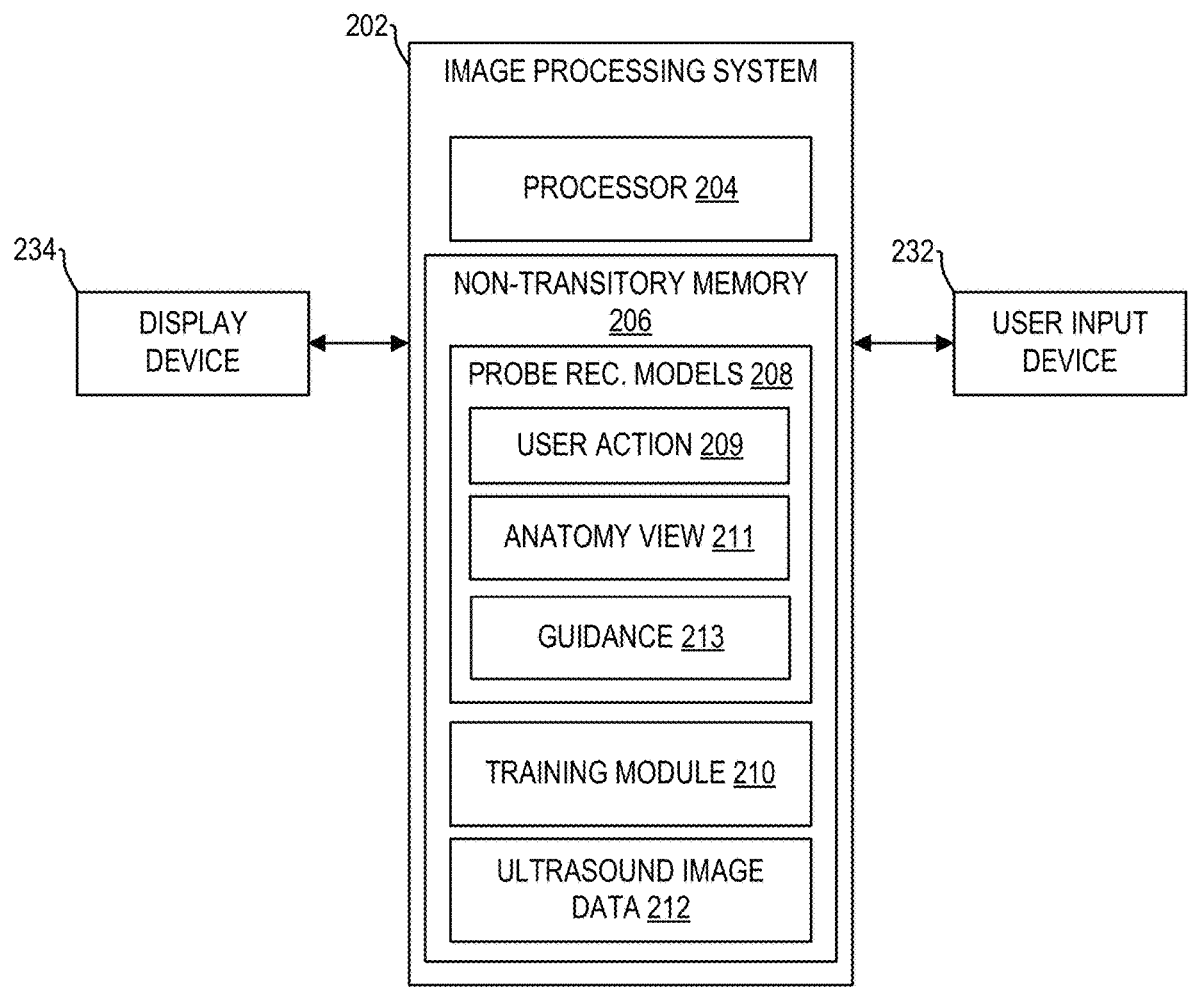
FIG. 2 is a schematic diagram illustrating a system for generating probe motion recommendations, according to an embodiment.
Figure 4A:
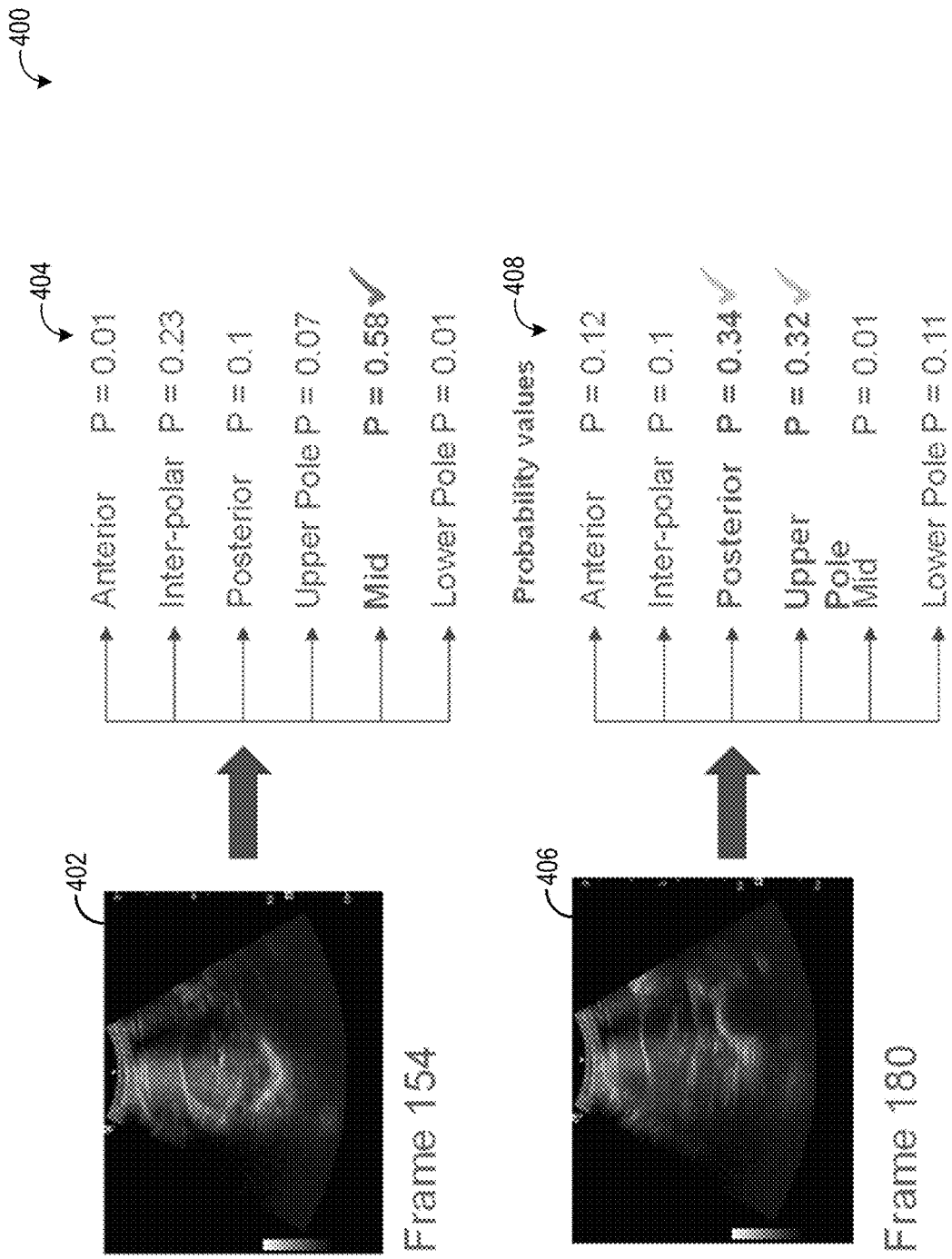
FIG. 4A shows example ultrasound images and associated anatomy view determinations, without using user action as an input.
Figure 4B:
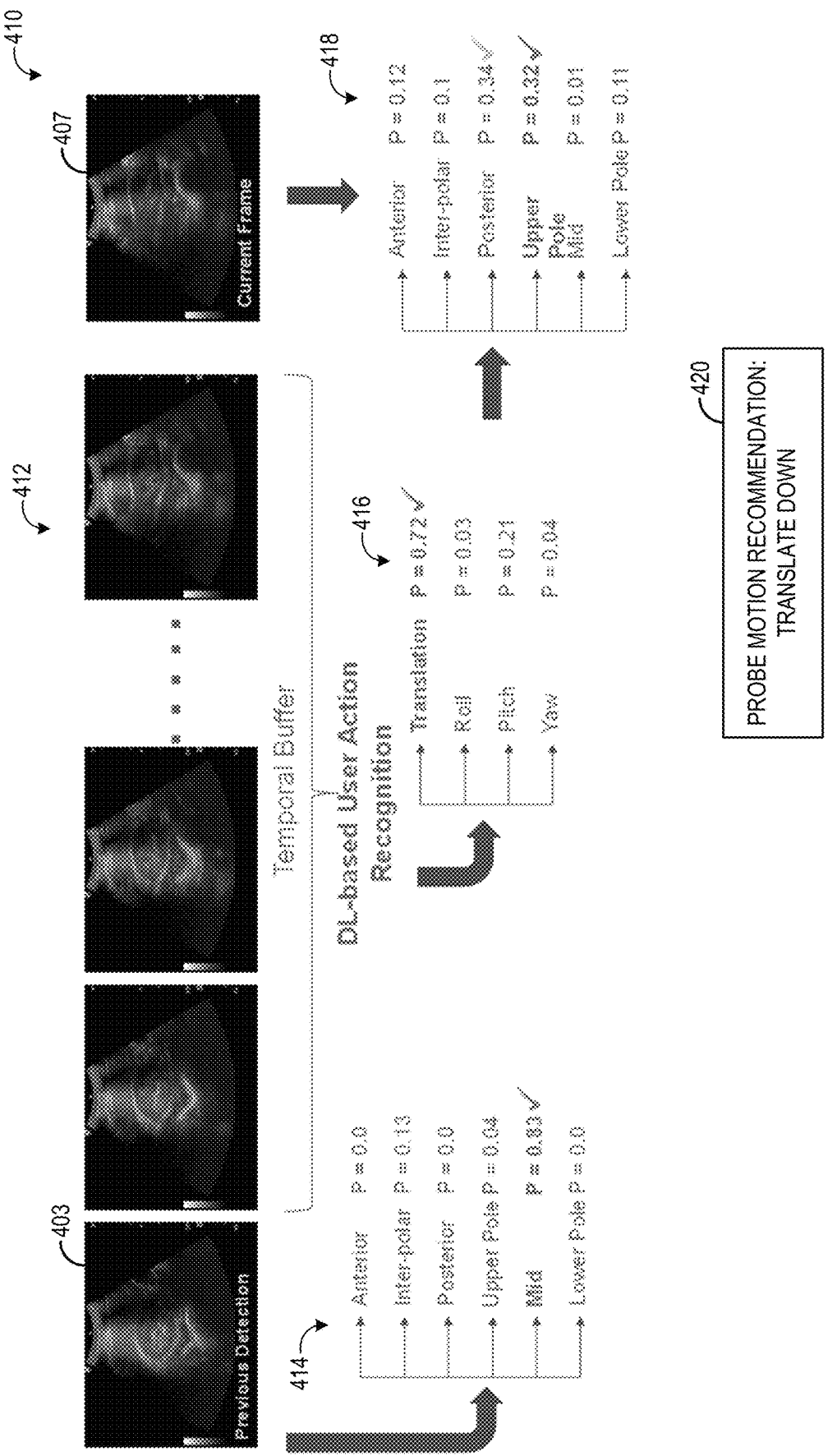
FIG. 4B shows example ultrasound images and associated anatomy view determinations, using user action as an input according to the process of FIG. 3.
Figure 5A:
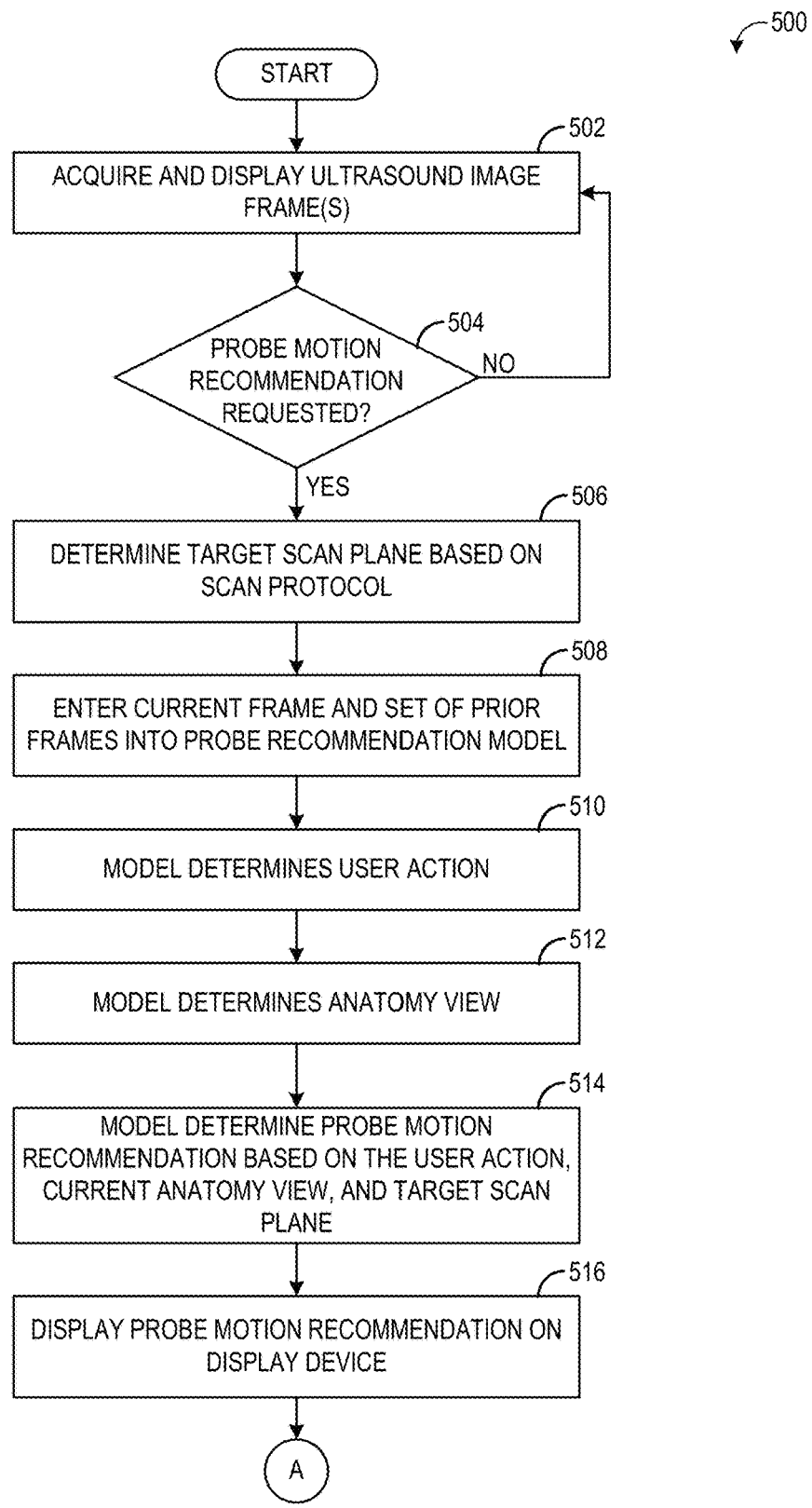
FIGS. 5A and 5B are a flow chart illustrating an example method for determining probe motion recommendations.
Figure 5B:
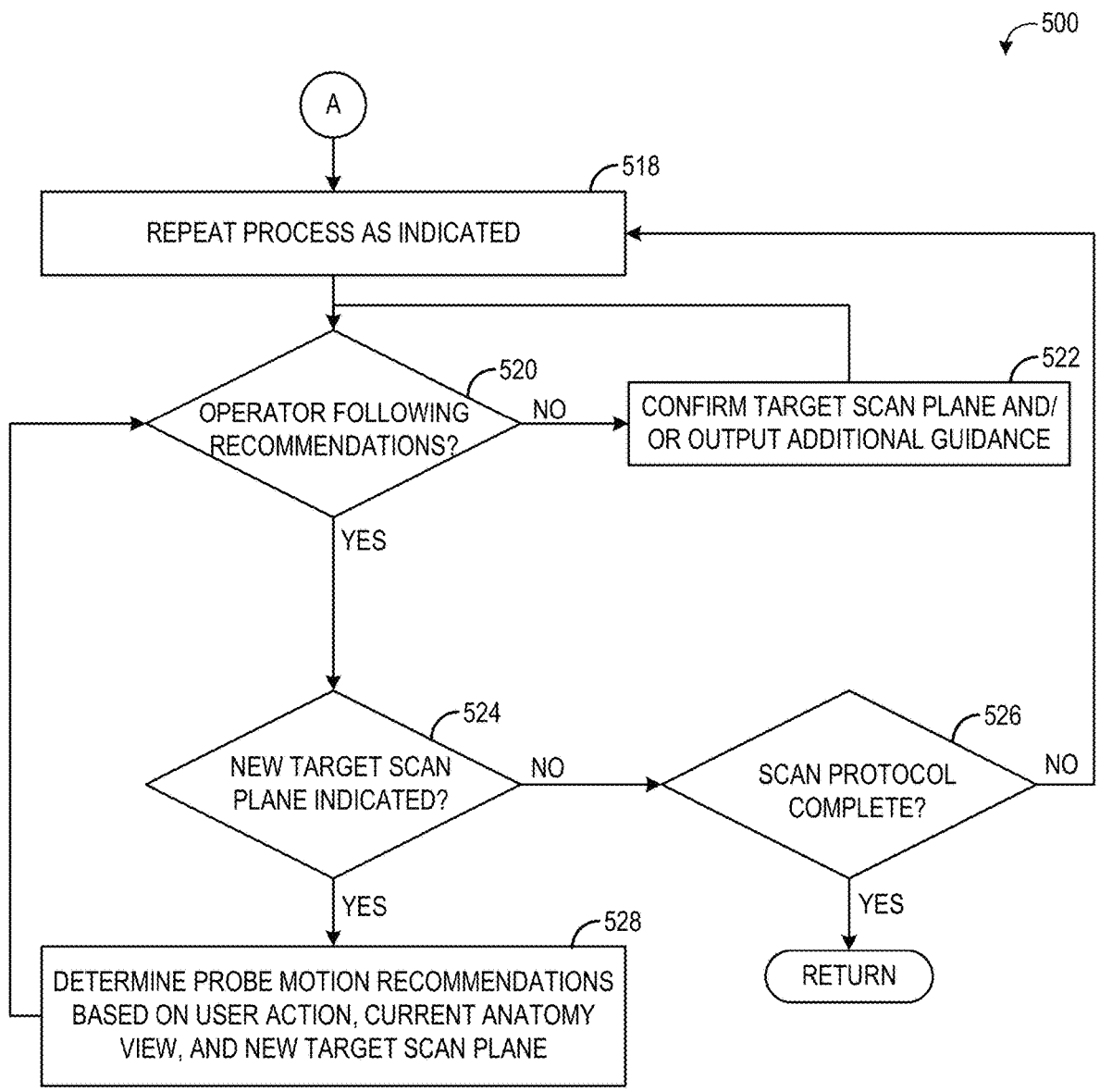

An example ultrasound system including an ultrasound probe, a display device, and an imaging processing system are shown in FIG. 1. Via the ultrasound probe, ultrasound images may be acquired and displayed on the display device. An image processing system, as shown in FIG. 2, includes one or more probe recommendation models, such as a user action model, an anatomy view model, and a guidance model, which may be deployed according to the process shown in FIG. 3 to determine probe motion recommendations. As shown in FIGS. 4A and 4B, when the user action (e.g., as determined by the user action model) is used as joint input along with the current anatomy view for determining probe motion recommendations, ambiguities in determining the current anatomy view may be resolved, which may result in more accurate and robust probe motion recommendations. A method for determining probe motion recommendations during ultrasound imaging is shown in FIGS. 5A and 5B. FIG. 6 shows example probe motion recommendations that may be displayed according to the methods/processes disclosed herein.

Referring to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. A variety of a geometries and configurations may be used for the transducer array (e.g., linear, convex, phased array) and the transducer array may be provided as part of, for example, different types of ultrasound probes, including but not limited to standard hand-held linear or curvilinear probes, endocavity probes, and cardiac probes. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. In one embodiment, data acquired via ultrasound system 100 may be used to train a machine learning model. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block.

Ultrasound images acquired by ultrasound imaging system 100 may be further processed. In some embodiments, ultrasound images produced by ultrasound imaging system 100 may be transmitted to an image processing system, where in some embodiments, the ultrasound images may be analyzed by one or more machine learning models trained using ultrasound images and corresponding ground truth output in order to estimate the current user action (e.g., the probe motion prior to and/or during acquisition of the current ultrasound image), the current anatomical view in the ultrasound image, and probe motion recommendations. As used herein, ground truth output refers to an expected or "correct" output based on a given input into a machine learning model. For example, if a machine learning model is being trained to classify images of cats, the ground truth output for the model, when fed an image of a cat, is the label "cat". As explained in more detail below, if a machine learning model is being trained to classify ultrasound images on the basis of the probe motion/user action occurring prior to and/or during acquisition of the ultrasound image, the ground truth output for the model may be a label indicating the probe motion/user action, e.g., a label indicating translation, rotation, etc. Similarly, if a machine learning model is being trained to classify ultrasound images on the basis of anatomical features in the ultrasound image, the ground truth output for the model may be a label indicating one or more anatomical features in the ultrasound image.

Although described herein as separate systems, it will be appreciated that in some embodiments, ultrasound imaging system 100 includes an image processing system. In other embodiments, ultrasound imaging system 100 and the image processing system may comprise separate devices. In some embodiments, images produced by ultrasound imaging system 100 may be used as a training data set for training one or more machine learning models, wherein the machine learning models may be used to perform one or more steps of ultrasound image processing, as described below.

Referring to FIG. 2, image processing system 202 is shown, in accordance with an exemplary embodiment. In some embodiments, image processing system 202 is incorporated into the ultrasound imaging system 100. For example, the image processing system 202 may be provided in the ultrasound imaging system 100 as the processor 116 and memory 120. In some embodiments, at least a portion of image processing system 202 is disposed at a device (e.g., edge device, server, etc.) communicably coupled to the ultrasound imaging system via wired and/or wireless connections. In some embodiments, at least a portion of image processing system 202 is disposed at a separate device (e.g., a workstation) which can receive images/maps from the ultrasound imaging system or from a storage device which stores the images/data generated by the ultrasound imaging system. Image processing system 202 may be operably/communicatively coupled to a user input device 232 and a display device 234. The user input device 232 may comprise the user interface 115 of the ultrasound imaging system 100, while the display device 234 may comprise the display device 118 of the ultrasound imaging system 100, at least in some examples.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store probe recommendation models 208, training module 210, and ultrasound image data 212. Probe recommendation models 208 may include one or more machine learning models, such as deep learning networks, comprising a plurality of weights and biases, activation functions, loss functions, gradient descent algorithms, and instructions for implementing the one or more deep neural networks to process input ultrasound images. Probe recommendation models 208 may include trained and/or untrained neural networks and may further include training routines, or parameters (e.g., weights and biases), associated with one or more neural network models stored therein. In some examples, only a single probe recommendation model 208 may be included, where the probe recommendation model 208 may be trained in an anatomy-independent manner such that probe recommendations may be output by the probe recommendation model 208 for multiple scan protocols and/or for imaging multiple, different anatomical features. In other examples, more than one probe recommendation model 208 may be included, with each probe recommendation model 208 trained or specific to a particular scan protocol and/or a particular anatomical feature or set of anatomical features. For example, one probe recommendation model may be specific to imaging a kidney, another probe recommendation model may be specific to imaging a heart, etc.

Each probe recommendation model may generate multiple outputs for a given ultrasound image. For example, each probe recommendation model 208 may output a user action 209, an anatomy view 211, and guidance 213. The user action may include the maneuvering of the probe by an operator prior to and/or during acquisition of the image. The user action may include translation and/or rotation (roll, pitch, and yaw) of the ultrasound probe, which are usually determined using external sensors such as inertial motion units (IMUs). However, IMUs or other sensors may be expensive, prone to drift, take up packaging space in the ultrasound probe, or exhibit other issues that limit their usefulness in an ultrasound imaging environment. Thus, the probe recommendation model 208 may determine the user action/user motion of the ultrasound probe without external sensors. The probe recommendation model 208 may use as input two or more prior ultrasound image frames leading to the current ultrasound image, and in some examples may also use the current ultrasound image as input. This series of images may also be referred to as a cine or sequence of images. Based on the prior images, the probe recommendation model 208 may output the movement of the ultrasound probe in six degrees (e.g., translation in 3 dimensions as well as roll, pitch, and yaw).

The anatomy view 211 that is determined/output by the probe recommendation model 208 may include a current anatomical view (e.g., a scan plane or an anatomical region) for a current ultrasound image. For example, if the ultrasound image includes a kidney and/or is acquired as part of a scan protocol for imaging the kidney, the probe recommendation model 208 may be trained to determine if the input ultrasound image includes an anterior view of the kidney, an inter-polar view of the kidney, a posterior view of the kidney, an upper pole view of the kidney, a middle view of the kidney, a lower pole view of the kidney, or a view that does not include the kidney. In some examples, the anatomy view 211 may also include anatomical features identified in the current ultrasound image. For example, the anatomical features may be identified in the current ultrasound image using segmentation, and then the identified anatomical features may be used to determine the scan plane/anatomical region that is imaged in the current ultrasound image. As will be explained in more detail below, the user action 209 may increase the accuracy of the anatomy view determination and/or resolve certain ambiguities in the determination of the anatomy view.

The guidance 213 may include recommendations as to how an operator should move (or maintain in position) an ultrasound probe, from a current position at which a current ultrasound image was acquired, in order to obtain a subsequent image. The guidance may be for a specific imaging protocol, e.g., an imaging protocol for imaging a kidney. Accordingly, at least in some examples, the guidance may include recommendations on how to move/positon the ultrasound probe based on the current or next step in the imaging protocol.

Thus, the probe recommendation model 208 may be a deep learning network (e.g., neural network) that takes multiple frames (e.g., the current frame and a plurality of prior frames) as input and produces multiple outputs, including anatomical features, organ view, user action, and guidance. The network may be trained jointly with loss functions for all of these tasks. To determine the user action, the probe recommendation model 208 may be trained with ground truth that includes sets of ultrasound images annotated by an expert looking at last x milliseconds or second of the ultrasound image frames (e.g., video) or sensor based tracker for automation/speed, with the annotation including the user action. Frames from previous x milliseconds are part of the input to the network training. The user actions may be determined independent of the anatomy being imaged and may be determined based speckle characteristics and/or image features, although anatomy may provide context to determine user action, and thus in some examples the probe recommendation model may be trained to determine the user action taking the specific anatomy as input. If the model is unable to determine a user action on a particular anatomy, the model may be retrained/updated with suitable data. For both the determination of the anatomy view and the guidance that are determined/output by the probe recommendation model, expert-provided labels/annotations may be used to train the probe recommendation model and a respective suitable loss function will be added to the joint model being trained. The annotations may include an indication of the scan plane/anatomical features in each image, to train the model to determine the anatomy view. The annotations may include probe motion recommendations for a current anatomy view and/or user action along with a target scan plane to be reached.

Thus, the single probe recommendation model 208 (e.g., neural network) described herein may take as input the current ultrasound image and one or more prior ultrasound images (e.g., the previous 5-10 or more ultrasound images acquired before the current ultrasound image was acquired) and output the guidance for moving the ultrasound probe. Using a single/joint model rather three independent models (e.g., a user action model, an anatomy view model, and a guidance model) may provide multiple advantages. The single model may synthesize multiple tasks and use information that will reinforce the tasks mutually. Functionally there will be no orchestration needed as would be the case with three separate models. Also, the use of a single model may produce more robust output with fewer ambiguities, as many situations may occur in which three separate models/ networks may output non-unique solutions but these situations can be resolved uniquely with the use of a single model. Also, runtime, memory, maintenance, and performance may all be improved with the use of a single model relative to three separate models.

Further, while the probe recommendation model 208 has been described herein has using 2D ultrasound images as input, in some examples the probe recommendation model 208 may use 3D ultrasound data instead of or in addition to 2D images. For example, the anatomy view and the anatomical feature segmentation may be determined using 3D data (e.g., the most recent 3D volume of data acquired by the ultrasound probe). The user action may be determined in 4D (e.g., 3D volumes over time, where a plurality of 3D volumes acquired over a period of time are entered as input to the probe recommendation model 208). Further still, while the probe recommendation model 208 has been described herein as being trained to analyze ultrasound images to determine recommendations for movement of an ultrasound probe, a similar approach could be taken to generate recommendations for other imaging modalities, particularly hand-held or otherwise easily manipulated imaging modalities, such as optical imaging devices/visible light cameras (e.g., included as part of an endoscope), X-ray/fluoroscopy scanners, near infrared (NIR) spectroscopy scanners, and optical coherence tomography (OCT) scanners.

Non-transitory memory 206 may further include training module 210, which comprises instructions for training one or more of the machine learning models stored in probe recommendation models 208. In some embodiments, the training module 210 is not disposed at the image processing system 202. The probe recommendation models 208 thus include trained and validated network(s).

Non-transitory memory 206 may further store ultrasound image data 212, such as ultrasound images captured by the ultrasound imaging system 100 of FIG. 1. The ultrasound image data 212 may comprise ultrasound image data as acquired by the ultrasound imaging system 100, for example. The ultrasound images of the ultrasound image data 212 may comprise ultrasound images that have been acquired by the ultrasound imaging system 100 with different preceding probe motion/user actions and/or different anatomical features. Further, ultrasound image data 212 may store ultrasound images, ground truth output, iterations of machine learning model output, and other types of ultrasound image data that may be used to train the probe recommendation models 208, when training module 210 is stored in non-transitory memory 206. In some embodiments, ultrasound image data 212 may store ultrasound images and ground truth output in an ordered format, such that each ultrasound image is associated with one or more corresponding ground truth outputs. However, in examples where training module 210 is not disposed at the image processing system 202, the images/ground truth output usable for training the probe recommendation models 208 may be stored elsewhere.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

User input device 232 may comprise one or more of a touchscreen, a keyboard, a mouse, a trackpad, a motion sensing camera, or other device configured to enable a user to interact with and manipulate data within image processing system 202. In one example, user input device 232 may enable a user to make a selection of an ultrasound image to use in training a machine learning model, to indicate or label a position of an interventional device in the ultrasound image data 212, or for further processing using a trained machine learning model.

Display device 234 may include one or more display devices utilizing virtually any type of technology. In some embodiments, display device 234 may comprise a computer monitor, and may display ultrasound images. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view ultrasound images produced by an ultrasound imaging system, and/or interact with various data stored in non-transitory memory 206.

It should be understood that image processing system 202 shown in FIG. 2 is for illustration, not for limitation. Another appropriate image processing system may include more, fewer, or different components.

Figure 3:
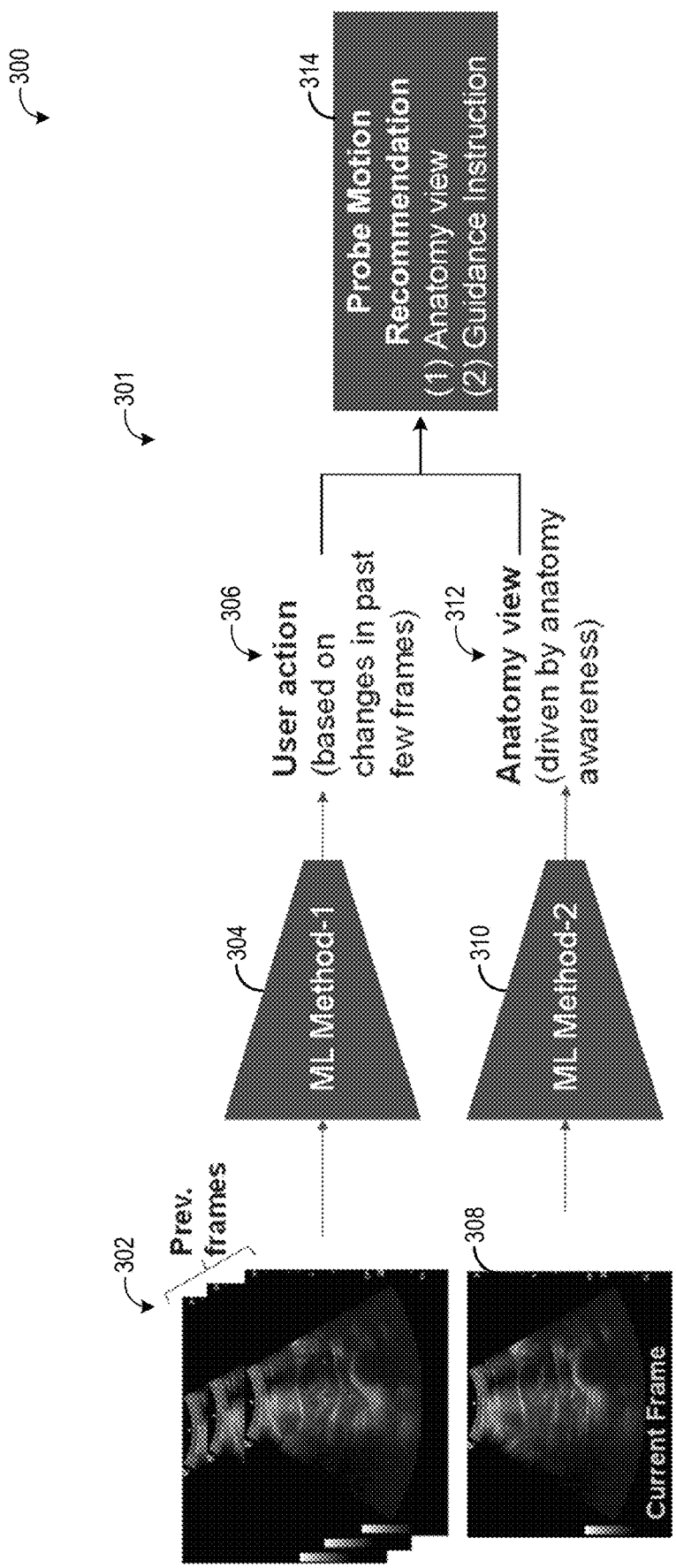
FIG. 3 is a schematic diagram illustrating a process for generating probe motion recommendations, according to an embodiment.

Turning to FIG. 3, it shows a process 300 for generating probe motion recommendations using a probe recommendation model 301. Process 300 may be implemented by the image processing system 202 of FIG. 2. Process 300 includes inputting a plurality of previous frames 302 to the probe recommendation model 301, which determines/outputs a user action 306 according to a first machine learning method 304. The plurality of previous frames 302 may include a suitable number of frames, such as 3, 5, 10, 20, or another number of frames, each acquired prior to a current frame 308. For example, the plurality of previous frames 302 may include the three (or more) immediately prior frames of ultrasound data acquired before the current frame 308 was acquired. As described above, the user action may include translation and/or rotation of the ultrasound probe, with translation including movement of the probe in three dimensions (e.g., superior-inferior, medial-lateral, anterior-posterior, etc.) and rotation including pitch, yaw, and/or roll of the probe. In some examples, the user action may include movement of the probe off the imaging subject.

Process 300 also includes inputting the current frame 308 into the probe recommendation model 301, which determines/outputs an anatomy view 312 via a second machine learning method 310. The anatomy view 312 of the current frame may include an identification of the anatomical feature(s) in the current frame (e.g., the kidney), a classification/category of the anatomical features in the current frame (e.g., upper pole of the kidney, selected from six possible regions of the kidney) and/or an imaging plane of the current frame (e.g., a four-chamber view of a heart). While FIG. 3 shows the first method 304 as being separate from the second method 310, it is to be understood that the methods are included in one single probe recommendation model. In this way, the second method 310 may utilize the current frame 308 and the user action applied prior to and/or during acquisition of the current frame 308 in order to determine the anatomy view of the current frame 308, at least in some examples.

Process 300 may include determining, with the probe recommendation model 301, probe motion recommendations 314 based on the user action 306 and the anatomy view 312. The probe motion recommendations 314 may include the anatomy view of the current frame and guidance instruction as to how to move the ultrasound probe in order to acquire a desired or target image for a given scanning protocol. The guidance instruction may include instructions to move the ultrasound probe in a particular manner (e.g., move up, move down, rotate left, etc.) or maintain the ultrasound probe in the current position. The guidance instructions and/or anatomy view may be output to an operator of the ultrasound probe, such as displayed on a display device (e.g., display device 234 and/or display device 118).

Some ultrasound scanning/imaging protocols may dictate that one or more particular anatomical views of a particular anatomical feature be imaged. For example, an ultrasound imaging protocol for imaging a kidney may dictate that a mid-transverse/mid-longitudinal scan-plane of the right kidney be imaged. An imaging system (e.g., the system 100 of FIG. 1) may output guidance to help an operator of an ultrasound probe navigate the ultrasound probe so that the mid-transverse/mid-longitudinal scan-plane of the right kidney is imaged. However, to provide actionable guidance, the ultrasound probe may first be positioned so that one of a plurality of predefined regions/scan planes is imaged, and then guidance can be provided. FIGS. 4A and 4B, described below, demonstrate the advantage that the user action detection brings to both anatomy view recognition and to providing actionable guidance.

FIG. 4A shows example anatomy view determinations 400 for two ultrasound image frames, a first frame 402 and a second frame 406, without considering the user action of the probe occurring during and/or prior to image acquisition. The anatomy view determinations 400 may be generated by an anatomy view model that determines the current anatomical view in an ultrasound image frame, based only on that ultrasound image frame (and without considering probe motion). As shown in FIG. 4A, when the first frame 402 is analyzed by the anatomy model, the model may generate, for each of a plurality of different anatomy views, a probability that the current frame includes that anatomy view. For example, as shown, a first set of probabilities 404 is generated, wherein the model determines the likelihood that the anatomy view of the first frame is an anterior kidney view, an inter-polar kidney view, a posterior kidney view, an upper pole kidney view, a mid-kidney view, or a lower pole kidney view. The probabilities indicate that the first frame is likely to be a mid-kidney view (e.g., as the probability for the mid-kidney view is greater than 50% and/or is greater than the other probabilities by at least a threshold amount). For example, the model may assign the relatively high probability to the mid-kidney view due to certain anatomical features being present and/or having certain visual features in the first frame 402 (e.g., rounded kidney, brighter Hilar portion in kidney center, and the liver being present above the kidney).

The second frame 406 may be obtained after the first frame 402, with multiple frames obtained between the first frame 402 and the second frame 406 (e.g., 15 frames may have been obtained between acquisition of the first frame 402 and acquisition of the second frame 406). During the time between acquisition of the first frame 402 and acquisition of the second frame 406, the ultrasound probe may be moved by the operator, resulting in a different anatomy view being present in the second frame 406. The second frame 406 may be input to the anatomy view model, which generates a second set of probabilities 408. The second set of probabilities 408 also indicates the likelihood that the second frame 406 includes one of the six kidney views discussed above. However, due to ambiguities in the anatomical features/visualizations as present in the second frame 406 (e.g., elongated kidney, faded Hilar region, and a small portion of the liver being present above the kidney), the model is not able to differentiate between the posterior view and the upper pole view of the kidney, which are each assigned a probability below 50% and within a threshold range of each other. Thus, the output of the anatomy view model may be inconclusive, as peripheral regions of the kidney (e.g., anterior/posterior and superior/inferior) can be visibly similar. Without knowing which region of the kidney is currently being imaged, actionable guidance may not be provided, or inaccurate guidance information may be provided.

FIG. 4B shows example anatomy view determinations 410 for two ultrasound image frames, where the user action of the probe occurring prior to acquisition of the second ultrasound image frame is used as input to determine probe motion recommendations and, in the example shown, differentiate between possible anatomy views imaged in the second ultrasound frame. The anatomy view determinations 410 may be generated by the probe recommendation model (e.g., probe recommendation model 208) that determines the current anatomical view in an ultrasound image frame, using that ultrasound image frame and the probe motion as determined by the probe recommendation model. As shown in FIG. 4B, when a previously detected frame 403 is analyzed by the probe recommendation model, the model may generate, for each of a plurality of different anatomy views, a probability that the current frame includes that anatomy view, as explained above with respect to FIG. 4A. For example, as shown, a third set of probabilities 414 is generated, indicating that the previously detected frame is likely to be a mid-kidney view (e.g., as the probability for the mid-kidney view is greater than 50% and/or is greater than the other probabilities by at least a threshold amount). No probe motion recommendations may be output based on the previously detected frame 403, as the previously detected frame 403 may be a first frame acquired before motion of the ultrasound probe and/or the previously detected frame 403 may include an image of a target scan plane and thus the operator may not need guidance to move to the target scan plane.

After acquisition of frame 403, the operator may move the ultrasound probe. Responsive to the motion of the ultrasound probe, a buffer of ultrasound image frames during motion of the probe may be formed or saved. The buffer may include a plurality of frames 412 that are acquired between the previously detected frame 403 and the current frame 407 (which in the example shown is the second frame 406 of FIG. 4A), during at least a portion of which the probe is being moved. The plurality of frames 412 are entered as input to the probe recommendation model, which outputs a fourth set of probabilities 416. The fourth set of probabilities 416 indicates the likelihood, for each of a plurality of different types of probe movements, that the user action of the probe preceding acquisition of the current frame 407 was that movement (e.g., translation, roll, pitch, and yaw). In the illustrated example, the probe recommendation model determines that the movement of the probe across the plurality of frames 412 is likely to be translation of the probe, as the probability for translation is greater than 50% and significantly larger than the other types of movements.

The current frame 407 is entered into the probe recommendation model. The probe recommendation model outputs a fifth set of probabilities 418, which may be the same as the second set of probabilities 408 of FIG. 4A and thus does not include a clear selection of an anatomy view (e.g., the upper pole and the posterior views are relatively equally likely). The probe recommendation model may use the fifth set of probabilities 418 and the fourth set of probabilities 416 to determine the probe motion recommendations/guidance, optionally along with the determination that the anatomy view for the previously detected frame 403 was a mid-kidney view. The inclusion of the user action (e.g., the translation) and the anatomy view of the previously detected frame 403 (e.g., the mid-kidney view) allows the probe recommendation model to select the upper pole view as the anatomy view. For example, because the probe moved from the mid-kidney view with a translation movement, the probe recommendation model was able to conclude the next view should be an upper pole or a lower pole view, and the visible anatomical features in the current frame indicate the upper pole view is more likely than the lower pole view. Because the current anatomy view is known (e.g., the upper pole view), actionable guidance to guide the operator to the target scan plane (e.g., the mid-transverse/mid-longitudinal scanplane of the right kidney) may be provided by the probe recommendation model. For example, a probe recommendation 420 may be output for display on a display device.

In the example shown in FIG. 4B, the selection of which frame to use to form the basis of the probe motion recommendations (e.g., which frame is entered to determine the anatomy view) may be based on the number of frames since a previous probe motion recommendation was determined and a selected frequency of the probe motion recommendations. For example, every fifteenth frame may be selected as the current frame and entered into the probe recommendation model as a first input, with a suitable number of preceding frames entered into the probe recommendation model as a second input (e.g., the prior 14 frames). In other examples, the selection of which frame to use as the basis of the probe motion recommendation may be based on the current probe motion ending. For example, once probe motion stops, an image frame acquired with a relatively stationary probe may be selected and entered into the probe recommendation model as the first input. In such an example, the system may determine that probe motion has stopped by analyzing frame to frame changes in anatomy and/or gradients in the images.

The number of preceding frames that are entered into the probe recommendation model as the second input may be a fixed number (e.g., based on a size of the buffer) or the number of preceding frames that are entered into the probe recommendation model as the second input may be variable based on the anatomy being imaged, the scan protocol, the speed or type of probe motion preceding the current frame, or other factors. Further, the preceding image frames that are stored in the buffer may be downsampled or otherwise adjusted to reduce storage space and allow more images to be saved and entered into the probe recommendation model, which may improve the accuracy of the user action estimation. For example, instead of saving each preceding image frame, every other preceding image frame may be saved.

FIGS. 5A and 5B are a flow chart illustrating an example method 500 for generating and outputting probe motion recommendations according to an embodiment of the present disclosure. Method 500 is described with regard to the systems and components of FIGS. 1-2, though it should be appreciated that the method 500 may be implemented with other systems and components without departing from the scope of the present disclosure. Method 500 may be carried out according to instructions stored in non-transitory memory of a computing device, such as image processing system 202 of FIG. 2.

At 502, ultrasound images are acquired and displayed on a display device. For example, the ultrasound images of a subject may be acquired with the ultrasound probe 106 of FIG. 1 and displayed to an operator via display device 118. The images may be acquired and displayed in real time or near real time, and may be acquired with default or user-specified scan parameters (e.g., default depth, frequency, etc.). At 504, method 500 determines if probe motion recommendations (e.g., guidance) have been requested. Probe motion recommendations may be requested by a user (e.g., the operator) via user input (e.g., a user may select a "recommendations" button on a graphical user interface), or probe motion recommendations may be requested automatically as part of a scan protocol that the operator may be following in order to image the subject. For example, the operator may select a scan protocol from a menu of scan protocols prior to or during imaging of the subject. The scan protocol may include a list of scan planes and/or anatomical features that are to be imaged, preset scan parameters that are applied to acquire the images, and/or other features. Further, the request to provide probe motion recommendations may include an indication of the anatomy that is being imaged or is to be imaged (e.g., the kidney).

If probe motion recommendations have not been requested, method 500 continues to acquire and display ultrasound image frames, until imaging is terminated by the operator or probe motion recommendations are requested. If probe motion recommendations are requested, method 500 proceeds to 506 to determine a target scan plane to be imaged based on the scan protocol. As explained above, the scan protocol may include one or more scan planes that are to be imaged and the target scan plane may be the next scan plane on the list of scan planes. However, in other examples, the target scan plane may be determined based on user input or another suitable mechanism.

At 508, the current frame (e.g., the most recently acquired image frame) and/or one or more prior frames (e.g., acquired before the current frame) are entered into a probe recommendation model. The probe recommendation model may be the probe recommendation model 208 of FIG. 2. The current frame may be entered into the probe recommendation model as a first input and the prior frames may be entered into the probe recommendation model as a second input. The prior frames may include frames that are temporarily stored in a buffer of the image processing system 202 and/or memory 120. The buffer may store a limited number of frames in a first in, first out manner (e.g., 15 frames), and thus the prior frames may include all the frames in the buffer or a subset of the frames in the buffer. The prior frames may be frames that are no longer being displayed and may or may not be saved in permanent storage. The current frame may be selected based on a frequency of generating probe motion recommendations (e.g., the frequency may be every fifteenth frame and the current frame may be the fifteenth frame since a previous recommendation was generated). In other examples, the current frame may be selected based on the current frame being a frame acquired while the probe was held stationary, with the prior frames acquired while the probe was being moved.

At 510, the probe recommendation model determines a user action. As explained previously, the probe recommendation model is trained to determine/output a user action that includes the movement of the ultrasound probe leading up to acquisition of the current frame, based on the prior frames. The user action may include translation and/or rotation of the ultrasound probe, with rotation including pitch, yaw, or roll. In some examples, the probe recommendation model may output one or more identified user actions. For example, if the probe recommendation model identifies the ultrasound probe was translated, the probe recommendation model may indicate that the user action is translation; if the probe recommendation model identifies that the ultrasound probe was both translated and rotated, the probe recommendation model may indicate that the user action is translation and rotation. In other examples, the probe recommendation model may output a probability that each of a plurality of actions were performed, as shown in FIG. 4B and described above. In some examples, the plurality of actions may include only single actions, while in other examples, the plurality of actions may include multiple actions that are performed simultaneously. The probe recommendation model may determine the user action without any sensor-based motion measurements (e.g., without measuring the position or motion of the probe with a sensor).

At 512, the probe recommendation model determines the anatomy view. The probe recommendation model may be trained to output the anatomy view shown in the current frame, using the current frame as input. The current anatomy view (e.g., the anatomy view of the current frame) may include one or more of identified anatomical features, an identified scan plane, and an identified anatomical region. In some examples, the probe recommendation model may output a probability for each of a plurality of anatomy views that indicates the likelihood the current frame includes that anatomy view, as shown in FIGS. 4A and 4B. In some examples, the probe recommendation model determines both an anatomy view and one or more anatomical features in the current frame, where the anatomy view includes an identified scan plane or anatomical region. For example, the probe recommendation model may first identify one or more anatomical features in the current frame, and then determine the anatomy view (e.g., an anatomical region) based on the one or more anatomical features, the positon(s) of the one or more anatomical features, brightness or other appearance parameters of the one or more anatomical features, and so forth.

At 514, the probe recommendation model determines/outputs one or more probe motion recommendations based on the user action, the current anatomy view (which may include both an anatomy view and one or more anatomical features), and the target scan plane. The probe motion recommendations may include guidance/recommendations for how the operator should move the probe in order to image the target scan plane, taking into consideration where the probe is currently located and how the probe is currently being manipulated. At 516, the probe motion recommendations are output to the operator by displaying the recommendations on a display device (e.g., display device 118). In some examples, additionally or alternatively, the probe motion recommendations may be output via an audible output mechanism (e.g., via a speaker), haptic feedback, or another suitable mechanism.

At 518 (continued on FIG. 5B), the above-described process of determining probe motion recommendations is repeated. The process may be repeated at a given frequency (e.g., for each Nth frame of ultrasound images). For example, after acquisition of the current frame, fifteen additional ultrasound frames may be acquired, and the fifteenth frame may be designated as the new current frame. The new current frame and the fourteen prior frames (or other subset of the prior frames) may be used to determine a new or updated probe motion recommendation according to the process described above, e.g., the prior frames and the new current frame may be entered as inputs to the probe recommendation model. Each time the determined probe motion recommendations change, updated recommendations may be output to the operator (e.g., displayed on the display device). In other examples, the process may be repeated each time motion of the probe is detected, or each time motion of the probe is detected and then the motion ends. In still further examples, the process may be repeated in response to a request to generate new probe motion recommendations.

At 520, method 500 includes determining if the operator is following the probe motion recommendations. The operator may be determined to be following the probe motion recommendations when, after outputting one or more probe motion recommendations, subsequent user actions and anatomy views indicate that the probe was moved as recommended. The operator may be determined not to be following the probe motion recommendations when, after outputting one or more probe motion recommendations, subsequent user actions and anatomy views indicate that the probe was not moved as recommended. If it is determined that the operator is not following the probe motion recommendations, method 500 proceeds to 522 to confirm that the target scan plane is the correct target scan plane and/or output additional guidance. For example, if the operator is not following the probe motion recommendations, the operator may have decided to image a scan plane that is different than the target scan plane and thus the probe motion recommendations may be inaccurate. Thus, a notification may be output (e.g., to the display device) asking the operator to confirm the target scan plane. In some examples, additionally or alternatively, additional guidance may be output (e.g., to the display device) in order to help guide the operator to the target scan plane. For example, there may be multiple paths to get to the target scan plane. When user is not following the recommended probe motions, a different set/combination of probe motion recommendations (alternate mode) can be used to reach the same scan plane. In some examples, the frequency of the output probe motion recommendations may be increased to provide more granular recommendations. For example, rather than outputting probe motion recommendations every 15 frames, as explained above, the probe motion recommendations may be output every 10 frames. Further, in some examples, the operator may be instructed to stop the current probe motion/user action (e.g., "stop rotating the probe"), which may further assist the operator by notifying the operator of motion errors rather than simply providing guidance of where to move the probe. This may also include notifying the operator that the operator is not following the probe motion recommendations.

If at 520 it is determined that the operator is following the probe motion recommendations, method 500 proceeds to 524 to determine if a new target scan plane has been indicated, via user input and/or via the scan protocol. For example, once one or more images of the target scan plane have been obtained, the scan protocol may indicate additional image(s) be obtained in a different scan plane. If a new target scan plane has not been indicated, method 500 proceeds to 526 to determine if the scan protocol is complete. For example, the scan protocol may be complete if all target scan planes/anatomical features dictated by the scan protocol have been imaged and/or if the operator indicates via user input that the scan protocol is complete or that the current imaging session is done. If the scan protocol is complete, method 500 returns. If the scan protocol is not complete, method 500 returns to 518 to continue to acquire images, enter the images into the probe recommendation model, and output appropriate probe motion recommendations.

If at 524 it is determined that a new target scan plane has been indicated, method 500 proceeds to 528 to determine probe motion recommendations for guiding the operator to the new target scan plane, where the probe motion recommendations are determined based on the user action, the current anatomy view, and the new target scan plane, similar to the process for generating probe motion recommendations for the previous target scan plane as described above. Upon outputting the probe motion recommendations, method 500 returns to 520 to determine if the operator is following the probe motion recommendations. In this way, probe motion recommendations may be generated for each target scan plane of the scan protocol, until scanning is complete.

Turning now to FIG. 6, it schematically shows a process 600 for generating example probe recommendations that may be output for display according to embodiments of the present disclosure. Process 600 includes an image 602 schematically showing an imaging subject. Superimposed on the image 602 is an ultrasound probe, indicating a first position 604 of the probe at a first time (time T1) and a second position 606 of the probe at a second time (time T2). A method for generating probe motion recommendations may be performed in order to guide an operator of the ultrasound probe to image a kidney 607 of the imaging subject.

Process 600 includes a first set of recommendations 610 that are determined without taking into account the user action of the probe. As shown in FIG. 6, at time T1, the anatomy view indicates that the lower pole of the kidney is being imaged. Based on the anatomy view and the target scan plane (e.g., mid cross-section of the kidney), the probe motion recommendation that is output includes instructions to translate the probe in order to move the probe upwards. At time T2, the anatomy view indicates that no kidney is present, as the operator has moved the probe upward too much, thereby missing the kidney (as shown in image 602). The probe motion recommendation that is output at time T2 includes instructions to locate the kidney. However, such instructions may not be helpful, as the operator may not know where or how to move the probe in order to locate the kidney.

Thus, process 600 includes a second set of recommendations 620 that may be determined when the user action of the probe is taken into account. As shown in FIG. 6, at time T1, the anatomy view indicates that the lower pole of the kidney is being imaged and that the current user action includes rotation of the probe. Based on the anatomy view, the user action, and the target scan plane (e.g., mid cross-section of the kidney), the probe motion recommendation that is output includes instructions to translate the probe in order to move the probe upwards. At time T2, the anatomy view indicates that no kidney is present, as the operator has moved the probe upward too much, thereby missing the kidney (as shown in image 602). The user action indicates that the current action of the probe is that the probe was translated upward. Because the user action is known, the anatomy view (e.g., no kidney) may be placed into context, such that the system may determine that the probe is positioned above the kidney. As such, more actionable guidance may be output. Thus, the probe motion recommendation that is output at time T2 may include instructions to translate the probe down. In this way, knowing the user action leading to a view enables re-routing instead of re-setting/starting afresh. The second set of recommendations 620 may be output by the probe recommendation model discussed herein, e.g., probe recommendation model 208 of FIG. 2.

Thus, the probe motion recommendations based on both user action and anatomy view as disclosed herein may provide many advantages, including improved accuracy of anatomy view detection/classification. The user action also provides a strong prior for the expected view (resulting from the action), similar to a Kalman filter in signal processing. Further, using both user action and the anatomy view allows for improved user guidance. For example, the user action provides context for the best possible guidance. Additionally, the detected "user action" may be related to the user, which may reassure the user of the guidance algorithm. Further, the guidance algorithm can qualify user action on the provided guidance (like change in color, etc.), provide quantified guidance, and qualify probe movement e.g. rotate slowly, translate slowly if rapid movement is detected. The probe motion recommendations may re-affirm or re-direct the user if their performed action is in accordance or contrary to the provided guidance. For example, if the prescribed guidance is to rotate the probe and the user performs a translation, the guidance algorithm can alert user on the discrepancy. In another example, if the user performs both a translation and a rotation, then the guidance algorithm can alert the user to perform only one motion (e.g., the translation).

A technical effect of providing probe motion recommendations based on both a current user action of the probe and a current anatomy view (e.g., the view that is currently being imaged by the probe) is that more accurate probe motion recommendations may be provided without reliance on external hardware.

The disclosure also provides support for a method, comprising: determining, with a probe recommendation model, a user action to an ultrasound probe prior to and/or during acquisition of a current ultrasound image frame, one or anatomical features in the current ultrasound image frame, and an anatomy view of the current ultrasound image frame, and outputting, for display on a display device, a probe motion recommendation based on the user action, the one or more anatomical features, and the anatomy view. In a first example of the method, determining the user action comprises determining the user action based on two or more ultrasound image frames acquired before the current ultrasound image frame. In a second example of the method, optionally including the first example, the probe recommendation model comprises a deep learning network and wherein determining the user action based on the two or more ultrasound image frames comprises entering the two or more ultrasound image frames into the deep learning network, where the deep learning network is trained to output the user action based on the two or more ultrasound image frames. In a third example of the method, optionally including one or both of the first and second examples, determining the one or more anatomical features in the current ultrasound image frame comprises entering the current ultrasound image frame into the deep learning network, where the deep learning network is trained to segment the current ultrasound image frame in order to identify the one or more anatomical features. In a fourth example of the method, optionally including one or more or each of the first through third examples, determining the anatomy view of the current ultrasound image frame comprises entering the current ultrasound image frame into the deep learning network, where the deep learning network trained to output the one or more anatomical features based on the current ultrasound image frame. In a fifth example of the method, optionally including one or more or each of the first through fourth examples, the deep learning network is trained to output the probe motion recommendation based on the user action, the one or more anatomical features, and the anatomy view. In a sixth example of the method, optionally including one or more or each of the first through fifth examples, the user action comprises translation and/or rotation of the ultrasound probe, wherein the probe motion recommendation includes instructions to guide an operator of the ultrasound probe to image a target scan plane, and wherein visual representations of the user action, the anatomy view, and/or the one or more anatomical features are also output for display on the display device.

The disclosure also provides support for a system, comprising: a display device, and an image processing system configured with instructions in non-transitory memory that when executed cause the image processing system to: determine a user action to an ultrasound probe prior to and/or during acquisition of a current ultrasound image frame based on a sequence of ultrasound image frames acquired prior to the acquisition of the current ultrasound image frame, determine an anatomy view of the current ultrasound image frame and one or more anatomical features present in the current ultrasound image frame, determine a probe motion recommendation based on the user action, the anatomical view, the one or more anatomical features, and a target scan plane, and output, for display on the display device, the probe motion recommendation. In a first example of the system, the non-transitory memory stores a deep learning network configured to determine the probe motion recommendation based on the user action, the anatomy view, the one or more anatomical features, and the target scan plane. In a second example of the system, optionally including the first example, the deep learning network is further configured to determine the user action, the one or more anatomical features, and/or the anatomical view. In a third example of the system, optionally including one or both of the first and second examples, the user action comprises translation and/or rotation of the ultrasound probe, and wherein the user action is determined independently of a respective anatomical view in each ultrasound image frame of the sequence of ultrasound image frames. In a fourth example of the system, optionally including one or more or each of the first through third examples, the sequence of ultrasound image frames comprises two or more consecutively-acquired ultrasound image frames. In a fifth example of the system, optionally including one or more or each of the first through fourth examples, the probe motion recommendation includes a recommendation to stop the user action. In a sixth example of the system, optionally including one or more or each of the first through fifth examples, the probe motion recommendation is a first probe motion recommendation determined according to a frequency of probe motion recommendations, and wherein the instructions further cause the image processing system to compare the user action to a second probe motion recommendation determined before the first probe motion recommendation, and if the user action is different than the second probe motion recommendation, adjust the frequency of probe motion recommendations.

The disclosure also provides support for a method, comprising: displaying a first ultrasound image frame acquired with an ultrasound probe in a first position, responsive to the ultrasound probe being moved out of the first position, forming a buffer of ultrasound image frames acquired during movement of the ultrasound probe, upon the ultrasound probe reaching a second position, generating a probe motion recommendation based on the buffer of ultrasound image frames and without any sensor-based motion measurements of the ultrasound probe, and outputting the probe motion recommendation for display on a display device. In a first example of the method, the second position is a stationary position. In a second example of the method, optionally including the first example, no probe motion recommendation is generated or output based on the first ultrasound image frame. In a third example of the method, optionally including one or both of the first and second examples, generating the probe motion recommendation based on the buffer of ultrasound image frames comprises entering two or more ultrasound image frames of the buffer of ultrasound image frames as input to a deep learning network trained to determine a category of the movement of the ultrasound probe, and generating the probe motion recommendation based on the category of the movement of the ultrasound probe and an anatomical view of a current ultrasound image frame acquired with the ultrasound probe at the second position. In a fourth example of the method, optionally including one or more or each of the first through third examples, the deep learning network comprises an anatomy-specific deep learning network. In a fifth example of the method, optionally including one or more or each of the first through fourth examples, the category of the movement of the ultrasound probe comprises translation and/or rotation of the ultrasound probe.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising,"

"including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method, comprising:
    determining, with a probe recommendation model, a current user action to an ultrasound probe prior to and/or during acquisition of a current ultrasound image frame, one or more anatomical features in the current ultrasound image frame, and an anatomy view of the current ultrasound image frame;
    outputting, for display on a display device, a probe motion recommendation based on the current user action, the one or more anatomical features, the anatomy view, and a target scan plane;
    determining if an operator is following the probe motion recommendation;
    responsive to the operator following the probe motion recommendation, determining whether a new target scan plane has been indicated; and
    responsive to the operator not following the probe motion recommendation, confirming the target scan plane, and outputting, for the display on the display device, additional guidance,
    wherein the current user action comprises at least one of sliding, tilting, rocking, and rotating the probe, and
    wherein determining the current user action comprises determining, using the probe recommendation model, a probability of each of a plurality of current user actions, the probability determined only based on a plurality of ultrasound image frames acquired before the current ultrasound image frame,
    wherein the probe recommendation model comprises a deep learning network and wherein determining the current user action further comprises entering the plurality of ultrasound image frames into the deep learning network, where the deep learning network is trained to output the current user action based on the plurality of ultrasound image frames.

2. The method of claim 1, wherein the current user action is just prior to the acquisition of the current ultrasound image frame, wherein determining the anatomy view of the current ultrasound image frame further comprises determining a probability for each of a plurality of anatomy views, wherein the anatomy view of the current ultrasound image frame includes an anatomy view generated by the probe recommendation model based on the one or more anatomical features, the position(s) of the one or more anatomical features, and brightness of the one or more anatomical features, and wherein the probe motion recommendation is based on the probability of each of a plurality of current user actions and the probability for each of a plurality of anatomy views that indicates the likelihood the current ultrasound image frame includes the anatomy view of the current ultrasound image frame including the anatomy view.

3. The method of claim 1, wherein determining the one or more anatomical features in the current ultrasound image frame comprises entering the current ultrasound image frame into the deep learning network, where the deep learning network is trained to segment the current ultrasound image frame in order to identify the one or more anatomical features.

4. The method of claim 1, wherein determining the anatomy view of the current ultrasound image frame comprises entering the current ultrasound image frame into the deep learning network, where the deep learning network trained to output the one or more anatomical features based on the current ultrasound image frame.

5. The method of claim 1, wherein the deep learning network is trained to output the probe motion recommendation based on the current user action, the one or more anatomical features, and the anatomy view.

6. The method of claim 1, wherein the current user action comprises rolling, pitching, and yawing of the ultrasound probe, wherein the probe motion recommendation includes instructions to guide the operator of the ultrasound probe to image the target scan plane, and wherein visual representations of the current user action, the anatomy view, and/or the one or more anatomical features are also output for display on the display device.

7. A system, comprising:
    a display device; and
    an image processing system configured with instructions in non-transitory memory that when executed cause the image processing system to:
        determine a current user action to an ultrasound probe prior to and/or during acquisition of a current ultrasound image frame based on a sequence of ultrasound image frames acquired prior to the acquisition of the current ultrasound image frame;
        determine an anatomy view of the current ultrasound image frame and one or more anatomical features present in the current ultrasound image frame;
        determine a probe motion recommendation based on the current user action, the anatomy view, the one or more anatomical features, and a target scan plane;
        output, for display on the display device, the probe motion recommendation;
        determine if an operator is following the probe motion recommendation;
        responsive to the operator following the probe motion recommendation, determine whether a new target scan plane has been indicated; and
        responsive to the operator not following the probe motion recommendation, confirm the target scan plane, and output, for the display on the display device, additional guidance,
    wherein the current user action comprises at least one of sliding, tilting, rocking, and rotating the probe, wherein determining the current user action comprises
determining, with the probe recommendation model,
a probability of each of a plurality of current user
actions, the probability determined only based on a
plurality of ultrasound image frames acquired before
the current ultrasound image frame, and wherein the probe recommendation model comprises a
deep learning network and wherein determining the
current user action further comprises entering the
plurality of ultrasound image frames into the deep
learning network, where the deep learning network is
trained to output the current user action based on the
plurality of ultrasound image frames.

8. The system of claim 7, wherein the non-transitory memory stores the deep learning network configured to determine the probe motion recommendation based on the current user action, the anatomy view, the one or more anatomical features, and the target scan plane.

9. The system of claim 8, wherein the deep learning network is further configured to determine the current user action, the one or more anatomical features, and/or the anatomy view.

10. The system of claim 7, wherein the current user action comprises rolling, pitching, and yawing of the ultrasound probe, and wherein the current user action is determined independently of a respective anatomical view in each ultrasound image frame of the sequence of ultrasound image frames.

11. The system of claim 7, wherein the sequence of ultrasound image frames comprises two or more consecutively-acquired ultrasound image frames.

12. The system of claim 7, wherein the probe motion recommendation includes a recommendation to stop the current user action.

13. The system of claim 7, further comprising responsive to the operator not following the probe motion recommendation, adjust a frequency of outputting the probe motion recommendations.

14. A method, comprising:
displaying a first ultrasound image frame acquired with an ultrasound probe in a first position;
responsive to the ultrasound probe being moved out of the first position, forming a buffer of ultrasound image frames acquired during movement of the ultrasound probe;
determining, with a probe recommendation model, a probability of each of a plurality of current user actions to the ultrasound probe, the probability determined only based on the buffer of ultrasound image frames;
upon the ultrasound probe reaching a second position, generating a probe motion recommendation based on the probability of each of the plurality of current user actions, a target scan plane, and without any sensor-based motion measurements of the ultrasound probe;
outputting the probe motion recommendation for display on a display device;
determining if an operator is following the probe motion recommendation;
responsive to the operator following the probe motion recommendation, determining whether a new target scan plane has been indicated; and
responsive to the operator not following the probe motion recommendation, confirming the target scan plane, and outputting, for the display on the display device, additional guidance,
wherein the plurality of current user actions comprises sliding, tilting, rocking, and rotating the probe, and
wherein the probe recommendation model comprises a deep learning network trained to determine a category of the movement of the ultrasound probe, and generating the probe motion recommendation based on the category of the movement of the ultrasound probe and an anatomical view of a current ultrasound image frame acquired with the ultrasound probe at the second position.

15. The method of claim 14, wherein the second position is a stationary position.

16. The method of claim 14, wherein no probe motion recommendation is generated or output based on the first ultrasound image frame.

17. The method of claim 14, wherein generating the probe motion recommendation based on the buffer of ultrasound image frames comprises entering two or more ultrasound image frames of the buffer of ultrasound image frames as input to the deep learning network.

18. The method of claim 17, wherein the deep learning network comprises an anatomy-specific deep learning network.

19. The method of claim 17, wherein the category of the movement of the ultrasound probe comprises translation and/or rotation of the ultrasound probe.

* * * * *